(12) United States Patent
Wahl et al.

(10) Patent No.: US 8,784,625 B2
(45) Date of Patent: Jul. 22, 2014

(54) SENSOR ELEMENT CONTAINING A SEALING ELEMENT FOR A FUNCTIONAL COMPONENT

(75) Inventors: Thomas Wahl, Pforzheim (DE); Georg Rixecker, Leinfelden-Echterdingen (DE); Steffen Polster, Stuttgart (DE); Uwe Glanz, Asperg (DE); Gudrun Oehler, Stuttgart (DE); Ulrich Eisele, Stuttgart (DE); Benjamin Hagemann, Gerlingen (DE); Alexander Bluthard, Stuttgart (DE); Frank Schnell, Kornwestheim (DE); Jochen Rager, Bisingen (DE); Petra Kuschel, Leonberg-Hoefingen (DE)

(73) Assignee: Robert Bosch GmbH, Stuttgart (DE)

( * ) Notice: Subject to any disclaimer, the term of this patent is extended or adjusted under 35 U.S.C. 154(b) by 867 days.

(21) Appl. No.: 12/737,158

(22) PCT Filed: Apr. 24, 2009

(86) PCT No.: PCT/EP2009/054955
§ 371 (c)(1),
(2), (4) Date: Mar. 24, 2011

(87) PCT Pub. No.: WO2009/153092
PCT Pub. Date: Dec. 23, 2009

(65) Prior Publication Data
US 2011/0162436 A1 Jul. 7, 2011

(30) Foreign Application Priority Data

Jun. 16, 2008 (DE) .......................... 10 2008 002 446

(51) Int. Cl.
*G01N 27/26* (2006.01)

(52) U.S. Cl.
USPC ............................................................ 204/426

(58) Field of Classification Search
USPC .................................. 204/425, 426; 73/23.2
See application file for complete search history.

(56) References Cited

U.S. PATENT DOCUMENTS

| | | | |
|---|---|---|---|
| 4,107,019 A | | 8/1978 | Takao et al. |
| 5,308,469 A | * | 5/1994 | Aldinger et al. ............. 204/426 |
| 5,474,665 A | * | 12/1995 | Friese et al. ..................... 431/2 |
| 5,827,415 A | * | 10/1998 | Gur et al. ...................... 204/426 |
| 6,613,207 B1 | * | 9/2003 | De La Prieta et al. ........ 204/426 |
| 6,719,950 B2 | * | 4/2004 | Day et al. ........................ 422/98 |

(Continued)

FOREIGN PATENT DOCUMENTS

| CN | 1288649 | 3/2001 |
|---|---|---|
| DE | 198 51 966 | 5/2000 |

(Continued)

*Primary Examiner* — Lisa Caputo
*Assistant Examiner* — Punam Roy
(74) *Attorney, Agent, or Firm* — Kenyon & Kenyon LLP

(57) ABSTRACT

A sensor element having a layered construction and configured to detect a physical property of a gas or a liquid includes a functional component situated in the interior, which functional component is connected electrically to a conductor element, which conductor element extends up to the outer surface or up into the surroundings of the sensor element. The sensor element has at least one sealing element which adjoins the functional component and/or the conductor element. The conductor element and the at least one sealing element are configured to be gas-tight at least regionally in the interior of the sensor element and are situated in such a way that the functional component is separated gas-tight from the surroundings of the sensor element.

9 Claims, 6 Drawing Sheets

(56) References Cited

U.S. PATENT DOCUMENTS

| | | | |
|---|---|---|---|
| 7,037,415 B2 * | 5/2006 | Cramer et al. | 204/429 |
| 7,083,710 B2 * | 8/2006 | Scheer et al. | 204/427 |
| 7,799,192 B2 * | 9/2010 | Wahl et al. | 204/424 |
| 7,943,025 B2 * | 5/2011 | Ohly et al. | 204/429 |
| 7,972,489 B2 * | 7/2011 | Stahl et al. | 204/428 |
| 2004/0040846 A1 * | 3/2004 | Heimann et al. | 204/426 |
| 2004/0182705 A1 * | 9/2004 | Ishikawa et al. | 204/424 |
| 2005/0155859 A1 * | 7/2005 | Schumann et al. | 204/426 |
| 2005/0160793 A1 | 7/2005 | Schumann et al. | |
| 2008/0269043 A1 * | 10/2008 | Wahl et al. | 501/136 |
| 2008/0289961 A1 * | 11/2008 | Schmitt et al. | 204/424 |

FOREIGN PATENT DOCUMENTS

| | | |
|---|---|---|
| DE | 10 2004 025 949 | 12/2005 |
| GB | 2 316 178 | 2/1998 |
| JP | 2005-33809 | 2/2005 |

\* cited by examiner

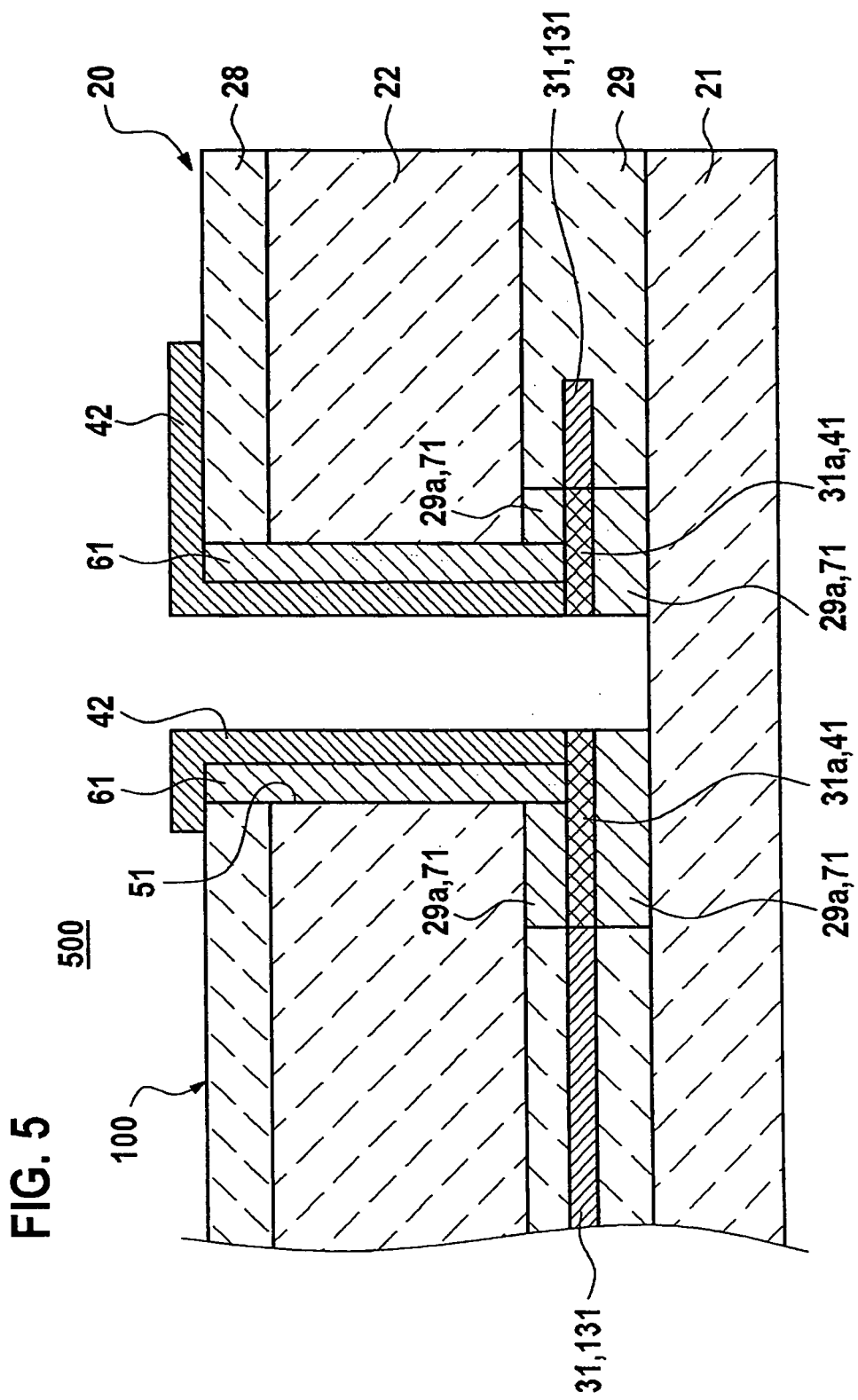

SENSOR ELEMENT CONTAINING A SEALING ELEMENT FOR A FUNCTIONAL COMPONENT

BACKGROUND OF THE INVENTION

1. Field of the Invention

The present invention is directed to a sensor element containing a sealing element for a functional component.

2. Description of Related Art

A sensor element having a layered construction is known, for example, from published German patent application document DE 10 2004 025 949 A1, and has a printed conductor, which extends from an outer side of the sensor element through a feedthrough up into the interior of the sensor element. A cover layer is situated in the area of the feedthrough in such a way that a gas located outside the sensor element may only reach the interior of the sensor element via a diffusion path, which at least regionally runs parallel to the outer surface of the sensor element. A sensor element constructed in this way has the advantage that contaminants do not accumulate or only accumulate substantially less in the interior of the sensor element.

Such a sensor element has the disadvantage that access of a gas which is located outside the sensor element, in particular an oxygenated exhaust gas or ambient air, to the functional component, which is situated in the interior of the sensor element, is possible, which results there in oxidative processes in particular at high temperatures, which may impair the function of the sensor element and contribute to premature aging and to the failure of the sensor element. These problems occur more extensively the baser and thus more reactive the material of the functional component. On the other hand, the use of such materials is attractive for cost reasons.

BRIEF SUMMARY OF THE INVENTION

The sensor element according to the present invention has the advantage over the related art in that an access of a gas, which is located outside the sensor element, to the functional component is not possible, and therefore oxidation of the functional component may be prevented even at high temperatures and while employing base materials. For this purpose, the conductor element and the sealing element in the interior of the sensor element are at least regionally designed as gas-tight and are situated in such a way that the functional component is separated gas-tight from the surroundings of the sensor element.

BRIEF DESCRIPTION OF THE DRAWINGS

FIG. 5 shows a cross-sectional view of an end section of another example embodiment of a sensor according to the present invention.

DETAILED DESCRIPTION OF THE INVENTION

Figure 1:
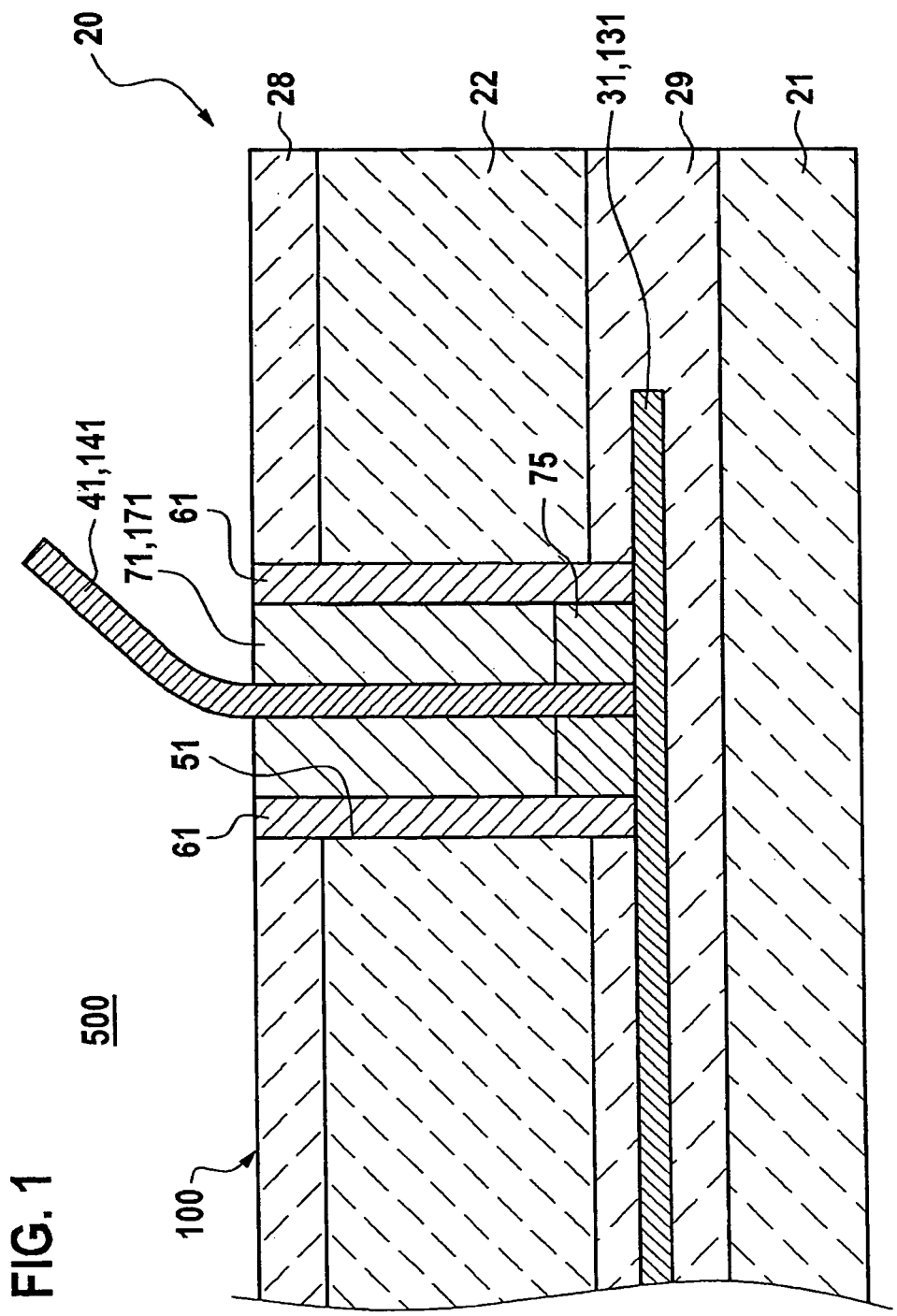
FIG. 1 shows a cross-sectional view of an end section of an example embodiment of a sensor according to the present invention.

As a first exemplary embodiment of the present invention, FIG. 1 shows a connection-side end section of a sensor element 20, which is situated in a housing of a gas sensor (not shown) and is used, for example, for determining the oxygen concentration in an exhaust gas of an internal combustion engine (not shown) or the temperature of the exhaust gas.

Sensor element 20 is constructed from ceramic layers 21, 22, 28, 29, of which two are formed as a first and a second solid electrolyte film 21, 22 and contain yttrium-oxide-stabilized zirconium oxide (YSZ) and two are formed as an outer and an inner printed, electrically insulating layer 28, 29 and contain aluminum oxide.

First and second solid electrolyte films 21, 22 are located above and below inner printed electrically insulating layer 29. Outer printed electrically insulating layer 28 is situated above second solid electrolyte film 22. Of course, the sensor element may have further layers for implementing functionalities of sensor element 20 which are known per se. These further layers may be made of ceramic material, for example.

A functional component 31, which is composed of an electrical resistance heater and a supply line 131 to the electrical resistance heater, is located inside inner printed electrically insulating layer 29. The electrical resistance heater causes, together with external wiring (not shown), the heating of sensor element 20 to temperatures up to significantly greater than 650° C. Supply line 131 to the electrical resistance heater extends up to the connection-side end section of sensor element 20, while the electrical resistance heater is situated in the diametrically opposing, measurement-side end section of sensor element 20 (not shown in FIG. 1). The material of which functional component 31 is made in this example has a high palladium proportion, for example, a proportion of greater than 50 percent by weight. Alternatively, other materials which also oxidize at temperatures greater than 650° C. in the presence of oxygen come into consideration.

Since the material, of which functional component 31 is made in this example, oxidizes at the operating temperatures of functional component 31 of greater than 650° C. in the presence of oxygen, it is provided that functional component 31 is separated gas-tight from surroundings 500 of sensor element 20.

In the area of the connection-side end section, sensor element 20 has a feedthrough 51 which extends, starting from functional component 31, through parts of inner printed electrically insulating layer 29, through second solid electrolyte film 22, and through outer printed electrically insulating layer 28 up to outer surface 100 of sensor element 20. The feedthrough has the form of a circular cylinder having a diameter of 0.3 mm to 1.5 mm, preferably 0.5 mm to 1.2 mm, whose axis is perpendicular to layers 21, 22, 28, 29. Of course, it would also be possible to give the footprint of feedthrough 51 an oval or polygonal shape and/or to situate feedthrough 51 at a different angle to layers 21, 22, 28, 29. A gas-tight, electrical insulation 61, which contains aluminum oxide, aluminum-magnesium spinel, or forsterite, for example, and has a thickness of 2 μm-100 μm, preferably 5 μm-50 μm, is applied to the wall of feedthrough 51, which is in the form of a cylindrical jacket. Insulation 61 thus has the form of a hollow cylinder.

A conductor element 41 is connected electrically conductive to functional component 31 in feedthrough 51 and in the interior of the hollow cylinder which is formed by insulation 61 with the aid of a conductive fixing attachment 75, an electrically conductive and mechanically fixing compound.

Conductor element 41 is a platinum wire 141, which extends inside feedthrough 51 along its axis and up into surroundings 500 of sensor element 20. Platinum wire 141 has a diameter of 50 μm-250 μm and has a gas-tight design. The remaining space of feedthrough 51, i.e., the space in the interior of the hollow cylinder formed by insulation 61, which is not occupied by conductive fixing attachment 75 or by platinum wire 141, is filled up by a sealing element 71, which is made of a gas-tight and electrically insulating glass or glass-ceramic compound 171. Glass or glass-ceramic compound 171 is $SiO_2$-based or phosphate-based having further proportions of $Al_2O_3$, MgO, CaO, and/or $B_2O_3$. Furthermore, glass or glass-ceramic compound 171 may contain proportions of ZnO, SrO, BaO, $La_2O_3$, $TiO_2$, and $Na_2O$ totaling less than 50 percent by weight, preferably less than 10 percent by weight. The coefficient of thermal expansion of employed glass or glass-ceramic compound 171 is between $4.5*10^{-6}$/K and $12*10^{-6}$/K for reasons of adaptation to the thermal expansion of the surrounding ceramics.

Thick-layer processes which are known per se are used for producing sensor element 20 according to the first exemplary embodiment, for example, screen printing, transfer printing, and through suction processes. Glass or glass-ceramic compound 171 is dispensed, prepared in powdered form, which is unpressed or pressed into shape, or in paste form, into feedthrough 51 and fired using a subsequent heating process, glass or glass-ceramic compound 171 becoming gas-tight through fusion and subsequent solidification. The firing temperature of the employed glasses is in the range from 900° C.-1400° C. The fired glass or the fired glass ceramic is high-temperature resistant and has a glass transition point of greater than 750° C.

Figure 2:
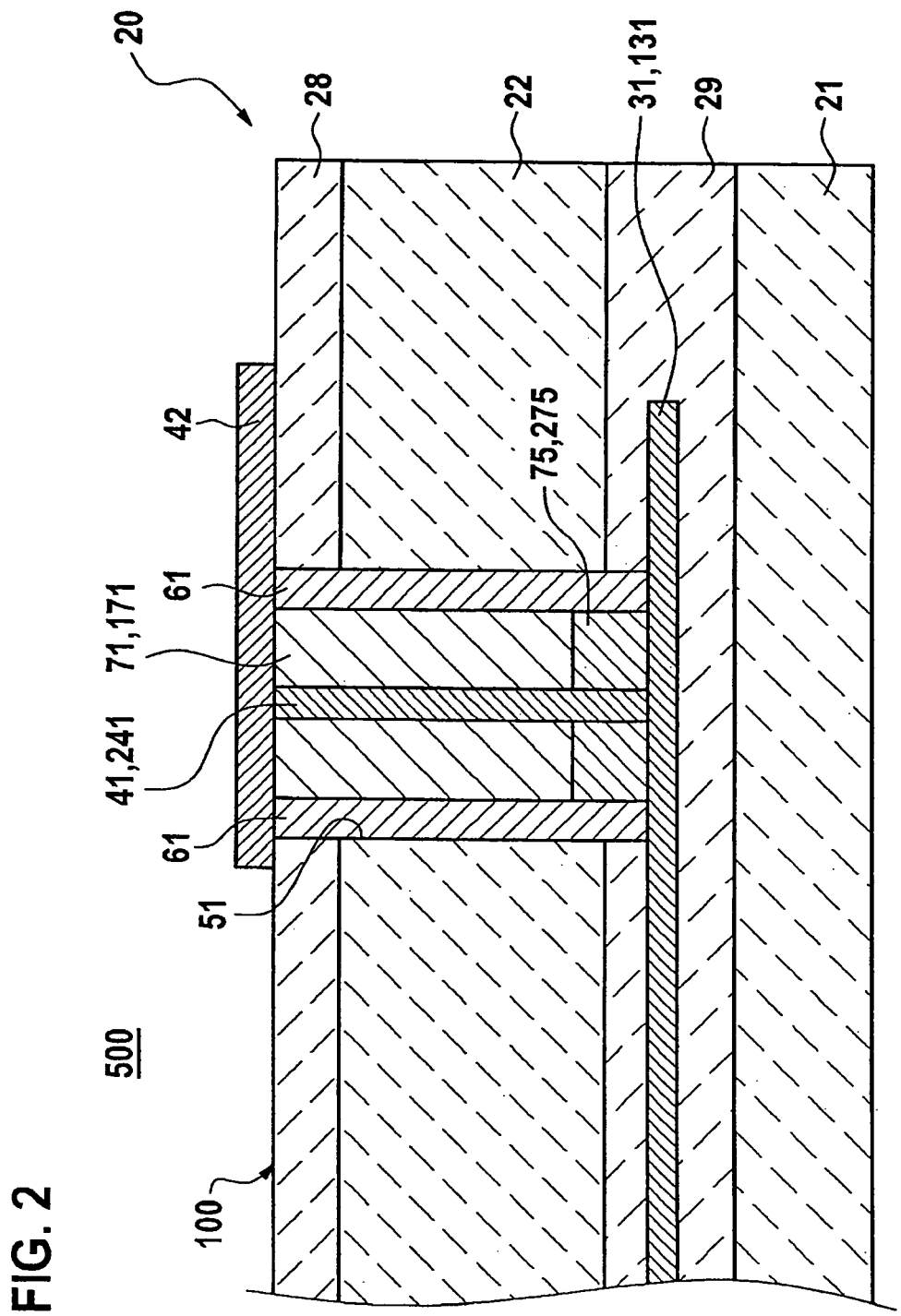
FIG. 2 shows a cross-sectional view of an end section of another example embodiment of a sensor according to the present invention.

FIG. 2 shows a second exemplary embodiment of the present invention, which differs from the first exemplary embodiment in that conductor element 41 is designed as a metal core 241. Metal core 241 has the form of a circular cylinder having a diameter of 80 μm-400 μm and terminates flatly with outer surface 100 of sensor element 20, like sealing element 71. Metal core 241 is connected mechanically and electrically conductive with the aid of a conductive fixing attachment 75 to functional component 31, as in the first exemplary embodiment of platinum wire 141, or a ductile metal layer 275 made of gold or nickel, which is 10 μm-200 μm thick, is located between metal core 241 and functional component 31. Metal core 241 contains platinum or nickel or is made of a chromium-nickel steel and has a gas-tight design.

A planar contact element 42, which is connected mechanically and electrically conductive to metal core 241, and is used for contacting the sensor element with an analysis and/or supply unit (not shown), is situated on outer surface 100 of sensor element 20.

Figure 3:
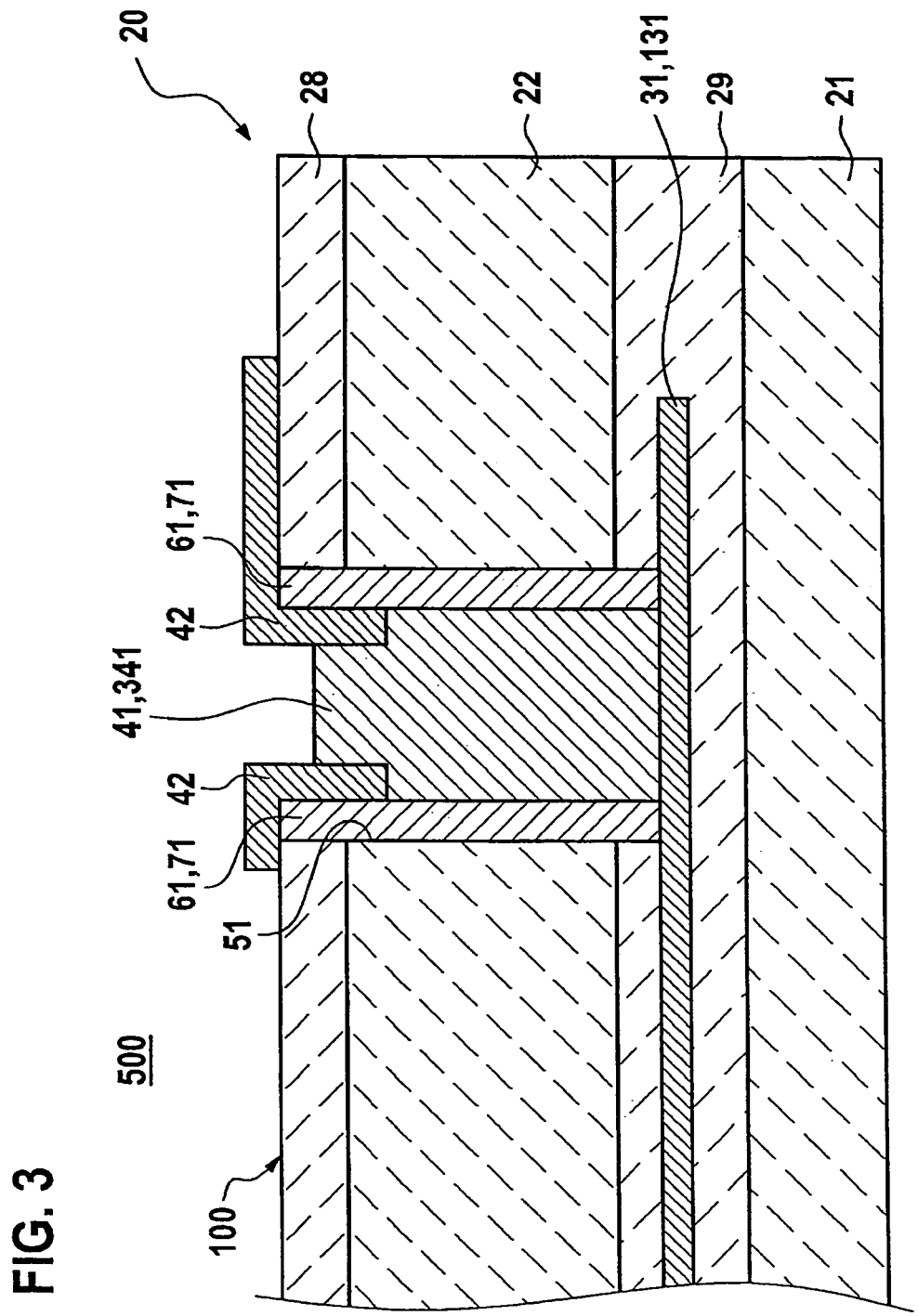
FIGS. 3 and 3a show a cross-sectional view of an end section of another example embodiment of a sensor according to the present invention.
Figure 3A:
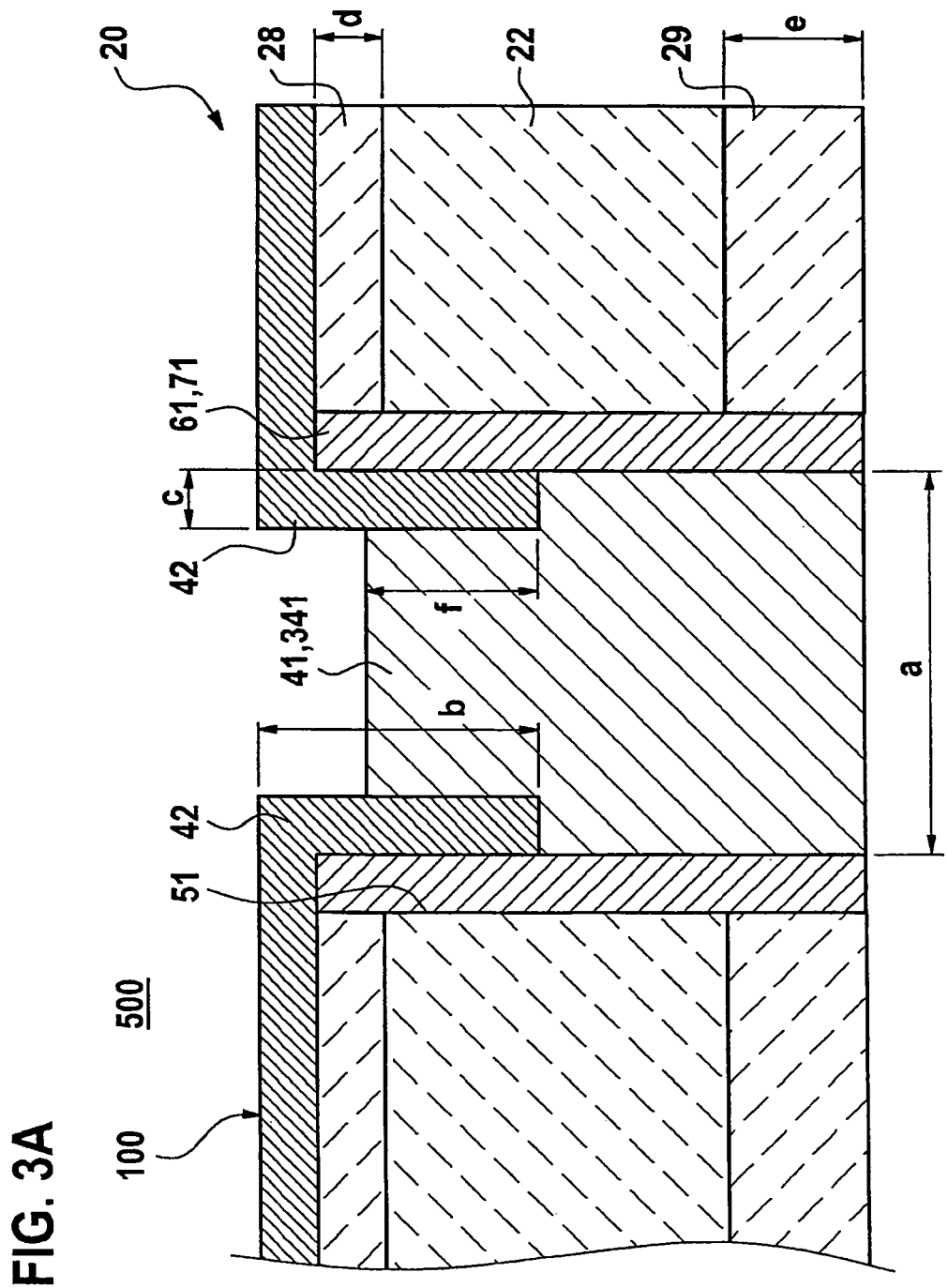

FIGS. 3 and 3a show a third exemplary embodiment of the present invention, which differs from the second exemplary embodiment in that contact element 42 is not only situated on outer surface 100 of sensor element 20, but rather also protruding into feedthrough 51 and into the interior of the hollow cylinder formed by insulation 61. Insulation 61 is composed and positioned as in the preceding examples, and is gas-tight in particular and takes over the function of sealing element 71 in this exemplary embodiment. Conductor element 41 includes a gas-tight, conductive filling 341 in this exemplary embodiment, which is connected electrically conductive to contact element 42 and to functional component 31. Gas-tight, conductive filling 341 fills up the entire cross-section of feedthrough 51, together with insulation 61, below the protrusion of contact element 42. Gas-tight, conductive filling 341 is made of a material which contains 5-90 percent by volume, preferably 10-50 percent by volume, platinum or platinum group metals (nickel, palladium, platinum) and also a glass or glass ceramic phase, whose composition corresponds to the composition of glass or glass ceramic compound 171 of the first exemplary embodiment, for example, and optionally contains alloy elements having a low sintering point, such as gold or silver. Filling 341 has a closed porosity.

In FIG. 3a, dimension a is the diameter of the hollow cylinder formed by insulation 61, dimension b is the length of the protrusion of contact element 42 into the interior of the hollow cylinder formed by insulation 61, dimension c is the width of this protrusion, dimension d is the thickness of layer 28, dimension e is the thickness of layer 29, and dimension f is the length of the protrusion of contact element 42 into gas-tight, conductive filling 341. Dimensions a, b, c, d, e, and f are selected as follows: a=900 μm, b=190 μm, c=30 μm, d=25 μm, e=45 μm, and f=135 μm. Alternatively, the dimensions are selected within the following limits: 300 μm<a<1500 μm, 20 μm<b<300 μm, 2 μm<c<100 μm, 5 μm<d<50 μm, 5 μm<e<70 μm, 20 μm<f<300 μm, preferably: 500 μm<a<1200 μm, 100 μm<b<200 μm, 5 μm<c<50 μm, 20 μm<d<30 μm, 40 μm<e<50 μm, 50 μm<f<200 μm.

Figure 4:
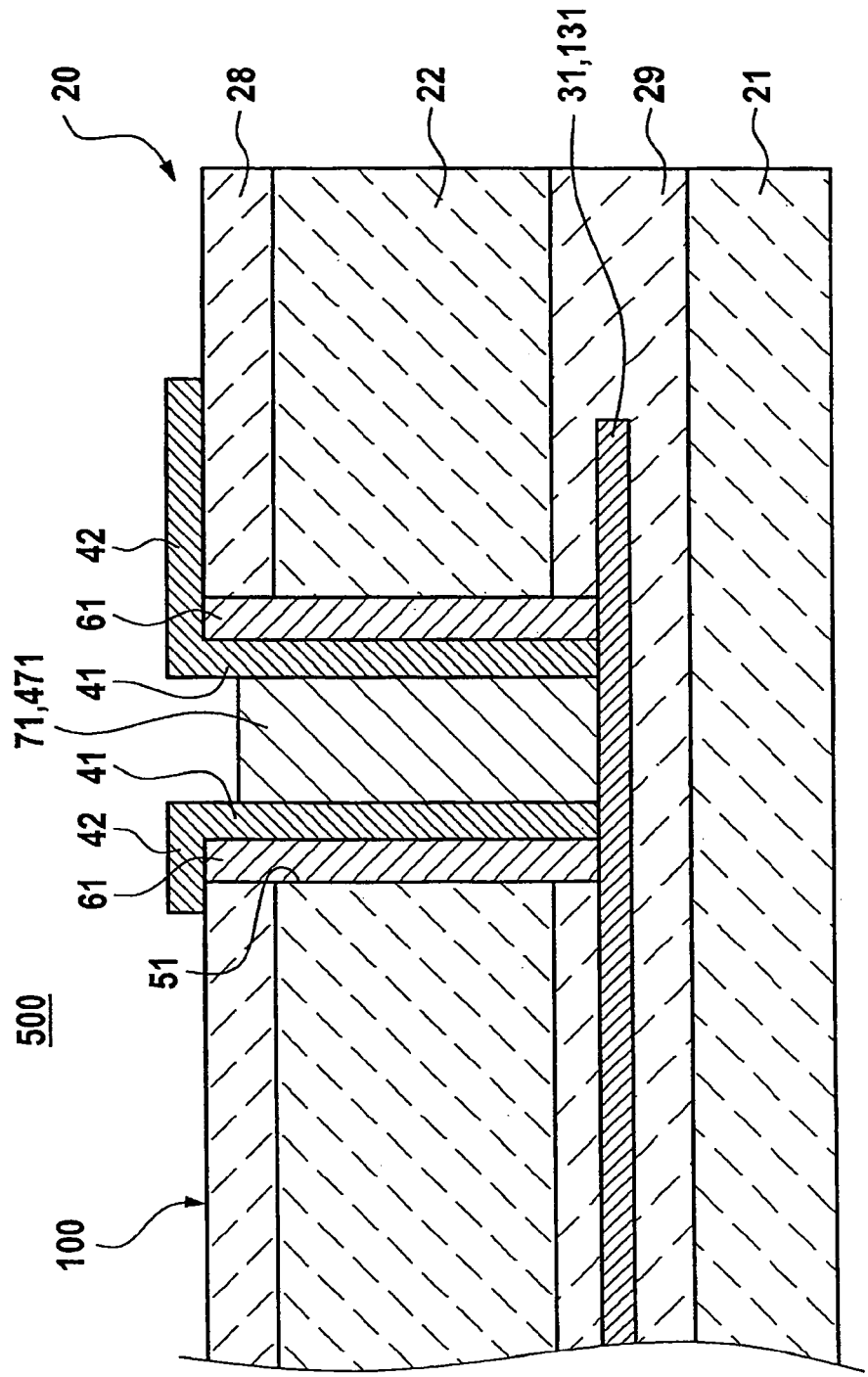
FIG. 4 shows a cross-sectional view of an end section of another example embodiment of a sensor according to the present invention.

FIG. 4 shows a fourth exemplary embodiment of the present invention, which differs from the third exemplary embodiment in that the protrusion of contact element 42 extends up to the base of feedthrough 51 and is connected electrically conductive there to functional component 31. The protrusion of contact element 42 has a gas-tight design and takes over the function of conductor element 41 in this exemplary embodiment and is designed as a hollow cylinder. The interior of the protrusion of contact element 42 is filled up by sealing element 71, which is made up of a glass or glass-ceramic compound 471 in this example. The composition of glass or glass-ceramic compound 471 corresponds to the composition of glass or glass-ceramic compound 171 from the first exemplary embodiment. The part of contact element 42 which is situated on outer surface 100 has a thickness of 2 μm-100 μm, preferably 5 μm-25 μm in this exemplary embodiment.

In an alternative specific embodiment of exemplary embodiments 1 through 4, layer 22 is made up of a gas-tight, electrically insulating material, which predominantly contains aluminum oxide and has a closed porosity, for example. Layer 22 takes over the function of sealing element 71 in this variant and conductor element 41 may be led through layer 22 in direct contact therewith. Insulation 61 may be dispensed with in this case.

The gas-tight separation of functional component 31 from surroundings 500 of sensor element 20 may also take place in that conductor element 41 runs at least partially within the same layer plane as functional component 31 and is gas-tight there, and sealing element 71 is situated at least partially within the same layer plane as a layer 29, which encloses functional component 31, and is gas-tight there. It is advantageously possible in this case to achieve a gas-tight separation of functional component 31 from surroundings 500 of sensor element 20 without a feedthrough 51 through sensor element 20 which is used for contacting functional component 31, having to be gas-tight. The fifth exemplary embodiment of the present invention, which is based on this idea, is shown in FIG. 5.

FIG. 5 shows a connection-side end section of a sensor element 20, which is situated in a housing of a gas sensor (not shown) and is used, for example, for determining the oxygen concentration in an exhaust gas of an internal combustion engine (not shown) or the temperature of the exhaust gas.

Sensor element 20 is constructed from ceramic layers 21, 22, 28, 29, of which two are designed as a first and a second solid electrolyte film 21, 22 and contain yttrium-oxide-stabilized zirconium oxide (YSZ) and two are designed as an outer and an inner printed, electrically insulating layer 28, 29 and contain aluminum oxide.

First and second solid electrolyte films 21, 22 are located above and below inner printed electrically insulating layer 29. Outer printed electrically insulating layer 28 is situated above second solid electrolyte film 22.

A functional component 31, which is composed of an electrical resistance heater and a supply line 131 to the electrical resistance heater, is located inside inner printed electrically insulating layer 29. The electrical resistance heater causes, together with an external wiring (not shown), the heating of sensor element 20 to temperatures greater than 650° C. Supply line 131 to the electrical resistance heater extends at least close to the connection-side end section of sensor element 20, while the electrical resistance heater is situated in the diametrically opposing, measurement-side end section of sensor element 20 (not shown in FIG. 5). The material of which functional component 31 is made of in this example has a high palladium proportion, for example, a proportion of greater than 50 percent by weight.

In the area of its connection-side end section, sensor element 20 has a feedthrough 51, which extends from the layer plane in which functional component 31 is located up to outer surface 100 of sensor element 20. A gas-tight, electrical insulation 61 is applied to the wall of feedthrough 51, in the form of a cylindrical sheath.

A contact element 42 extends from outer surface 100 of sensor element 20 along the inner side of insulation 61 up to the layer plane in which functional component 31 lies. Contact element 42 is designed as a hollow cylinder inside feedthrough 51 with an interior remaining free. Contact element 42 is connected electrically conductive to functional component 31.

Since the material of which functional component 31 is made of oxidizes in the presence of oxygen at operating temperatures of functional component 31 of greater than 650° C., functional component 31 is separated gas-tight from surroundings 500 of sensor element 20.

For this purpose, a part 29*a* of inner electrically insulating printed layer 29 is gas-tight in an area situated laterally around feedthrough 51. This part 29*a* of inner electrically insulating printed layer 29 takes over the function of sealing element 71. Furthermore, a gas-tight supply line 31*a*, preferably having high platinum content, which electrically connects contact element 42 and functional component 31 to one another, is located in the layer plane of functional component 31. This gas-tight supply line 31*a* takes over the function of conductor element 41. The gas-tightness of sealing element 71 and conductor element 41 is achieved by a closed porosity or by sintering additives of a glass or glass-ceramic phase or by adding alloy elements which sinter at low temperatures, such as gold or silver.

The area which is situated laterally around feedthrough 51 extends, starting from the outer edge of feedthrough 51, to a width of between 300 µm and 5000 µm. In one specific embodiment it may also be provided that functional component 31 and gas-tight supply line 31*a* overlap on a length of up to 1 mm.

All exemplary embodiments allow the use of a material which oxidizes under the influence of oxygen for functional component 31 at operating temperatures of up to greater than 650° C. This material may be a relatively cost-effective noble metal in comparison to platinum, such as palladium or gold.

Furthermore, the use of metals which are not noble metals is possible, such as nickel, tungsten, molybdenum, titanium, tantalum, niobium, iron, or chromium. For this purpose, it is to be noted that if these materials are used, oxidations of the materials used for the functional components are also to be prevented during the manufacturing process. For this purpose, in particular during the sintering procedure, the use of a reducing atmosphere is advantageous, in particular the gases argon and nitrogen having a volume proportion of up to 5% hydrogen.

If materials are used for functional component 31 which react with aluminum oxide, for example, various metals (atomic type Me) do this, in that they react to form $MeAl_2O_4$ (spinel) at high temperatures, direct contact between functional component 31 and aluminum oxide is to be prevented, for example, by providing a diffusion barrier layer. In the case of nickel, it may be made of zirconium oxide, for example. Since the coefficient of thermal expansion of the relevant materials sometimes significantly deviates from the coefficient of thermal expansion of the employed ceramics, it may be advantageous for the material of which functional component 31 is made of to have a ceramic second phase (cermet), whereby it is possible to bring the coefficients of thermal expansion into harmony.

A further possibility is the use of carbon in the form of carbon nanotubes as the material for functional component 31. The material containing the carbon nanotubes is advantageously processed as a paste for this purpose, for example, with the aid of screenprinting. A debinding of this paste may be performed in an oxygenated atmosphere, the sintering process is to be performed in a protective gas atmosphere. Since material containing carbon nanotubes having a high specific conductance is presently only available to a limited extent, it may be advantageous to use materials in functional components 31 which have carbon in the form of carbon nanotubes (for example, as a heating resistor of an electrical heater) in addition to other materials (for example, having platinum in the supply lines of this heater). If the heating resistor of an electrical heater is constructed by carbon in the form of carbon nanotubes, the possibility exists of designing this heating resistor as planar, for example, in an area whose edge lengths are greater than 2 mm.

What is claimed is:

1. A sensor element for detecting one of a concentration of a gas component or a temperature of an exhaust gas of an internal combustion engine, comprising:
 a functional component situated in interior portion of the sensor element and between a first ceramic layer and a second ceramic layer;
 a conductor element, wherein the functional component is connected electrically conductive to the conductor element, and wherein the conductor element extends one of (i) up to an outer surface of the sensor element or (ii) up into surroundings of the sensor element, and wherein at least a portion of the conductor element extends at least partially within the same layer plane as the functional component and is gas-tight; and
 at least one sealing element adjoining at least one of the functional component and the conductor element, wherein at least a portion of the sealing element is situated at least partially within the same layer plane as a layer at least partially enclosing the functional component and is gas-tight;
 wherein the conductor element and the at least one sealing element are (i) configured to be gas-tight at least regionally in the interior of the sensor element and (ii) situated in such a way that the functional component is separated in a gas-tight manner from the surroundings of the sensor element, and (iii) are at least partially situated and gas-tight between the first and the second ceramic layers and (iv) positioned in such a way that the functional component is separated gas-tight from the surroundings of the sensor element, and wherein the sensor element has a layered construction.

2. The sensor element as recited in claim 1, wherein the functional component is at least one of an electrical resistance heater and a supply line to an electrical resistance heater.

3. The sensor element as recited in claim 1, wherein the functional component contains a material which oxidizes in the presence of oxygen at a temperature of 650° C., the material being at least 50 percent of the functional component by weight.

4. The sensor element as recited in claim 1, wherein the functional component includes one of a noble metal, a base metal, or a carbon nanotube, wherein the one of the noble metal, the base metal, or the carbon nanotube is at least 50 percent of the functional component by weight.

5. The sensor element as recited in claim 1, wherein the gas-tight region of the conductor element has at least one of: (i) a closed porosity; (ii) an alloy element having one of gold or silver; (iii) a glass phase; and (iv) a glass-ceramic phase.

6. The sensor element as recited in claim 1, wherein the sensor element has a feed-through extending from the outer surface of the sensor element through at least one ceramic layer up to the plane of the functional component, and wherein at least one of the sealing element and the conductor element is at least partially situated inside the feed-through and gas-tight in a region inside the feed-through.

7. The sensor element as recited in claim 6, wherein the sealing element is situated on the inner side of the feed-through.

8. A sensor element for detecting one of a concentration of a gas component or a temperature of an exhaust gas of an internal combustion engine, comprising:
   a functional component situated in interior portion of the sensor element;
   a conductor element, wherein the functional component is connected electrically conductive to the conductor element, and wherein the conductor element extends one of (i) up to an outer surface of the sensor element or (ii) up into surroundings of the sensor element; and
   at least one sealing element adjoining at least one of the functional component and the conductor element, wherein:
   the conductor element and the at least one sealing element are (i) configured to be gas-tight at least regionally in the interior of the sensor element and (ii) situated in such a way that the functional component is separated in a gas-tight manner from the surroundings of the sensor element, and wherein the sensor element has a layered construction,
   the functional component is situated between a first ceramic layer and a second ceramic layer;
   the conductor element and the at least one sealing element are at least partially situated and gas-tight between the first and the second ceramic layers,
   the conductor element and the at least one sealing element are positioned in such a way that the functional component is separated gas-tight from the surroundings of the sensor element,
   the sensor element has a feed-through extending from the outer surface of the sensor element through at least one ceramic layer up to the plane of the functional component, and
   at least one of the sealing element and the conductor element is at least partially situated inside the feed-through and gas-tight in a region inside the feed-through, wherein the sealing element has a cavity, and wherein at least a part of the conductor element is situated in the interior of the cavity.

9. A sensor element for detecting one of a concentration of a gas component or a temperature of an exhaust gas of an internal combustion engine, comprising:
   a functional component situated in interior portion of the sensor element;
   a conductor element, wherein the functional component is connected electrically conductive to the conductor element, and wherein the conductor element extends one of (i) up to an outer surface of the sensor element or (ii) up into surroundings of the sensor element; and
   at least one sealing element adjoining at least one of the functional component and the conductor element, wherein:
   the conductor element and the at least one sealing element are (i) configured to be gas-tight at least regionally in the interior of the sensor element and (ii) situated in such a way that the functional component is separated in a gas-tight manner from the surroundings of the sensor element, and wherein the sensor element has a layered construction,
   the functional component is situated between a first ceramic layer and a second ceramic layer;
   the conductor element and the at least one sealing element are at least partially situated and gas-tight between the first and the second ceramic layers,
   the conductor element and the at least one sealing element are positioned in such a way that the functional component is separated gas-tight from the surroundings of the sensor element,
   the sensor element has a feed-through extending from the outer surface of the sensor element through at least one ceramic layer up to the plane of the functional component, and
   at least one of the sealing element and the conductor element is at least partially situated inside the feed-through and gas-tight in a region inside the feed-through, wherein the conductor element has a cavity, and wherein at least a part of the sealing element is situated in the interior of the cavity.

* * * * *